(12) United States Patent
Chen et al.

(10) Patent No.: US 10,126,156 B2
(45) Date of Patent: Nov. 13, 2018

(54) DEVICE AND METHOD FOR ONLINE MEASUREMENT OF GAS FLOWRATE AND LIQUID FLOWRATE OF WET GAS IN HORIZONTAL PIPE

(71) Applicant: Haimo Technologies Group Corp., Gansu (CN)

(72) Inventors: Jige Chen, Beijing (CN); Jianhua Xie, Gansu (CN); Guodong Wu, Gansu (CN); Bo Hu, Beijing (CN); Jie Chen, Gansu (CN); Junjie Ye, Gansu (CN)

(73) Assignee: HAIMO TECHNOLOGIES GROUP CORP., Lanzhou, Gansu (CN)

( * ) Notice: Subject to any disclaimer, the term of this patent is extended or adjusted under 35 U.S.C. 154(b) by 300 days.

(21) Appl. No.: 14/779,591

(22) PCT Filed: Apr. 25, 2014

(86) PCT No.: PCT/CN2014/076254
§ 371 (c)(1),
(2) Date: Sep. 24, 2015

(87) PCT Pub. No.: WO2014/194729
PCT Pub. Date: Dec. 11, 2014

(65) Prior Publication Data
US 2016/0076925 A1    Mar. 17, 2016

(30) Foreign Application Priority Data
Mar. 25, 2013 (CN) .......................... 2013 1 0097234

(51) Int. Cl.
*G01F 1/74* (2006.01)
*G01F 1/44* (2006.01)
(Continued)

(52) U.S. Cl.
CPC .................. *G01F 1/74* (2013.01); *G01F 1/42* (2013.01); *G01F 1/44* (2013.01); *G01N 23/12* (2013.01)

(58) Field of Classification Search
CPC ........................................................ G01F 1/74
See application file for complete search history.

(56) References Cited

U.S. PATENT DOCUMENTS

2007/0144268 A1\* 6/2007 Atkinson ............... G01N 23/12
                                                                 73/861.63
2009/0000390 A1\* 1/2009 Duhanyan ................. G01F 1/74
                                                                 73/861.04

FOREIGN PATENT DOCUMENTS

CN       1731105 A    2/2006
CN     102435245 A    5/2012
(Continued)

OTHER PUBLICATIONS

Bai, Linhai, "Research of Measurement Method of Oil-Water and Gas Multi Phase Flow," Chinese Doctoral Dissertations & Master's Theses Full Text Database (2006).

*Primary Examiner* — Manuel A Rivera Vargas
(74) *Attorney, Agent, or Firm* — Morgan, Lewis & Bockius LLP; Jeffry S. Mann

(57) ABSTRACT

The invention relates to a device for online measurement of gas flowrate and liquid flowrate of a wet gas in a horizontal pipe, comprising the following parts: a horizontal Venturi tube, comprising a truncated cone-shaped inlet pipesection with section area reduced gradually, a cylindrical throat pipesection and a truncated cone-shaped outlet pipesection with section area increased gradually; and a gamma ray monitor, comprising a gamma ray emitter and a gamma ray detector arranged in a manner that gamma rays emitted by the gamma ray emitter can radially pass through the cross section of the throat pipesection to reach the gamma ray (Continued)

detector. The invention also relates to a method for online measurement of gas flowrate and liquid flowrate of a wet gas in a horizontal pipe by using above device.

11 Claims, 11 Drawing Sheets

(51) Int. Cl.
    *G01F 1/42*     (2006.01)
    *G01N 23/12*     (2018.01)

(56) References Cited

FOREIGN PATENT DOCUMENTS

| CN | 202471152 U | 10/2012 |
| CN | 103292849 A | 9/2013 |

\* cited by examiner

DEVICE AND METHOD FOR ONLINE MEASUREMENT OF GAS FLOWRATE AND LIQUID FLOWRATE OF WET GAS IN HORIZONTAL PIPE

FIELD OF THE INVENTION

The invention is in the field of the multiphase flowrate metering. Particularly, the invention relates to a device for online measurement of gas flowrate and liquid flowrate of wet gas in a horizontal pipe, and to a method for online measurement of gas flowrate and liquid flowrate of wet gas in a horizontal pipe.

BACKGROUND OF THE INVENTION

In the oil-exploring industry, gas and liquid mixed fluids comprising liquid phase and gas phase are usually explored from oil wells, and the fluids are customarily called as "wet gas" in the art. The wet gas belongs to a multiphase flow in nature, that is, to be a mixed fluid of gas phase and liquid phase. Said gas phase includes, for example, oil field gas or any gases which are non-condensable at room temperature, wherein the oil field gas is generally relatively light alkanes, such as methane, ethane, propane, butane and the like. Said liquid phase may include: an oil phase, e.g., crude oil per se, and other liquid additives which are dissolved in crude oil during the exploration of crude oil; and a water phase, e.g., formation water, water which is injected into oil wells during the exploration, and other liquid additives which are dissolved in the water phase. The liquid volume flowrates and gas volume flowrates of gas and liquid mixed fluids explored from oil wells, which are real-time and accurately measured, are necessary basic data for production management and production optimization.

A first method relating to a device for measuring gas and liquid volume flowrate in a multiphase flow has the following working mechanisms: a gas and liquid mixed fluid is separated into a gas phase and a liquid phase via a separator. The separator generally achieves the gas and liquid separation by the means of the gravity force. Alternatively, the gas and liquid separation is achieved via a cyclone separator. Then, the volume flowrates of the gas phase and liquid phase can be respectively metered. However, because the separator and relevant instillations affiliated thereto weigh to be decadal tons, occupy a space having an area of hundreds square meters, and have many controlling links, maintenances and managements for the separator are complex, which is disadvantageous to automation of the management to production procedure, in particular, disadvantageous to the use in oil fields in desert and ocean. Furthermore, the method in which the liquid phase and the gas phase are separated from each other and then their flows are measured is not a real-time on-line measuring method, there is a hysteresis in the measurement.

A second method for online measurement of gas flowrate and liquid flowrate of wet gas is described as follows: a single phase meter is arranged horizontally along production pipelines for wet gas, and the wet gas is measured as a single phase. Since no multiphase meter is used, the liquid amount or an approximate value thereof should be known beforehand by other routes. Metering result of the single phase is deemed as the gas amount, while usually, the value is falsely high, and thus it should be corrected. A commonly-used correction method in the art is the interactive calculation based on the Lockhard-Martinelli parameter of gas phase and liquid phase, and a main representative of the calculation method is the ISO wet gas model, for example, please see ISO/TR 11583:2012, with the English title "Measurement of wet gas flow by means of differential pressure devices inserted in circular cross-section conduits", where all the corrections are directed to the gas amount. However, the method has three primary disadvantages: 1. there is on explicit dynamic mechanism; 2. only the gas amount is corrected, and no calculation and correction to the calculation of the liquid phase; and 3. the applicable scope of the method is only limited to a narrow range of the gas content of a fluid having a very high gas content.

A third method is concerned with a total flowrate metering device and phase fraction meter horizontally arranged along the production pipeline of wet gas, which can measure the total volume flowrate $Q_t$ and the gas linear phase fraction $\alpha_g$ along a certain radial direction of the horizontal pipe, respectively, and the following equations can be calculated: $Q_g = Q_t \times \alpha_g$; $Q_l = Q_t \times (1-\alpha_g)$, wherein $Q_t$ is the total volume flowrate; $Q_g$ is the gas volume flowrate; $Q_l$ is the liquid volume flowrate; and $\alpha_g$ is the gas linear phase fraction.

In the method, wet gas in the horizontal pipeline is generally assumed to be a mist fluid, that is, in a state wherein the liquid phase in the horizontal pipeline is uniformly dispersed in the gas phase in a form of droplets, and there is no slip difference between the liquid phase and the gas phase. Furthermore, the phase fraction meter in the method is generally arranged at a certain radial position of the horizontal pipe, and the measured gas phase fraction is the gas linear phase fraction $\alpha_g$ at the radical position. Since the above "homogenous phase" and "no slip difference" are hypothetically present, the measured gas linear phase fraction $\alpha_g$ is equivalent to the gas area phase fraction $\alpha_{sg}$ and the gas volume phase fraction GVF. The methods assumes that the wet gas in the horizontal pipe is a homogenous mist fluid and there is no slip difference between gas phase and liquid phase, which is not in line with the actual situation of the wet gas flow. In the horizontal pipe, due to impacts of gravity, systemic pressure and temperature, and the amount of the moisture in the wet gas, the wet gas is not an ideal homogenous state in the horizontal pipeline, and thus there is the error when using the gas linear phase fraction $\alpha_g$ along the radial direction of the horizontal pipe to replace the gas volume phase fraction GVF, and the impacts of the above factors on the measuring precision of the liquid phase are even more obvious. In the wet gas, GVF is a number close to 1, and minor variances in the GVF value will lead to a great relative error of the LVF, thereby to result in a great measuring error of the liquid phase flowrate. Thus, in the method, the measuring precision of the liquid phase is usually poor.

In a fourth method, the above measurements are carried out in a vertical pipeline, so as to avoid the deviation from the above "mist flow" hypothesis caused by the deposition of liquid phase on the bottom of the pipeline, wherein, all pipelines to be measured are arranged vertically. However, production pipelines of wet gas in oil field are usually horizontal, and thus the above measurements can be carried out only when the direction of the pipeline are changed from a horizontal orientation to a vertical direction. Thus, in the method, the direction of the pipeline should be changed and a transition pipeline should be arranged for stabilizing the flow pattern, so that the measurement device occupies a large space, which is disadvantageous to the arrangement of an oil and gas platform at sea which requires a high layout compactness.

Hence, there is a need in the art for a device and method which can online measuring gas flowrate and liquid flowrate of wet gas in a horizontal pipeline, which is not in need of changing the flowing direction of fluid, so that the measurement can be carried out by using a measuring device having short tube structure, and spaces occupied by the measuring device can be greatly reduced and the arrangement operations are simplified, while achieving a measuring precisions as high as possible.

SUMMARY OF THE INVENTION

A first aspect of the invention relates to a device for online measurement of gas flowrate and liquid flowrate of a wet gas in a horizontal pipe, comprising the following parts:

A horizontal Venturi tube, comprising a truncated cone-shaped inlet pipesection with section area reduced gradually, a cylindrical throat pipesection and a truncated cone-shaped outlet pipesection with section area increased gradually; and A gamma ray monitor, comprising a gamma ray emitter and a gamma ray detector arranged in a manner that gamma rays emitted by the gamma ray emitter can radially pass through the cross section of the throat pipesection to reach the gamma ray detector.

A second aspect of the invention relates to a method for online measurement of gas flowrate and liquid flowrate of a wet gas in a horizontal pipe, comprising the steps of:

a. Passing the wet gas through a segment of a horizontal Venturi tube, the horizontal Venturi pipe comprising a truncated cone-shaped inlet pipesection with section area reduced gradually, a cylindrical throat pipesection and a truncated cone-shaped outlet pipesection with section area increased gradually;

b. Measuring the radial linear phase fractions $\alpha_{g-\theta}$ of the gas phase along the cross section of the throat pipesection with a gamma ray monitor, the gamma ray comprising a gamma ray emitter and a gamma ray detector arranged in a manner that gamma rays emitted by the gamma ray emitter can radially pass through the cross section of the throat pipesection to reach the gamma ray detector; and c. Calculating gas phase flowrate $Q_g$ and liquid phase flowrate $Q_l$ with the total volume flowrate $Q_t$ and the above radial linear phase fractions $\alpha_{g-\theta}$ of the gas phase in accordance with an equal-diameter eccentric round model with the following specific equations:

Calculation of the eccentric distance d:

$$d = (R - 2R\alpha_{g-\theta})\sin\theta + \sqrt{R^2 - (R - 2R\alpha_{g-\theta})^2 \cos^2\theta}$$

Wherein R denotes the radius of the throat pipesection, and $\theta$ denotes the angle of the radial direction used during the measurement in relative to the horizontal radial direction;

Calculation of the area phase fraction $\alpha_{sg}$ of the gas phase:

$$\alpha_{sg} = \frac{4R^2 \cos^{-1}\left(\frac{d}{2R}\right) - \sqrt{(4R^2 - d^2)d^2}}{2\pi R^2};$$

Calculation of the volume phase fraction GVF of the gas phase:

$$GVF = \frac{\alpha_{sg} \times S}{\alpha_{sg} \times S + 1 - \alpha_{sg}}$$

wherein S denotes the slip difference between the gas phase and liquid phase; when the slip difference is taken into account, S is calculated by using experimental equations; when the slip difference is not taken into account, S=1, so $GVF = \alpha_{sg}$;

Calculation of the gas and liquid flowrates of the wet gas in the horizontal pipe:

$$Q_g = Q_t \times GVF$$

$$Q_l = Q_t \times (1 - GVF).$$

BRIEF DESCRIPTION OF THE DRAWINGS

FIG. 2B shows a method for determining the positions of points in the profile of the gas and liquid phase interface by taking the points B1, B2 and B3 as examples; FIG. 2C shows a conventional profile of a smooth and level interface of gas and liquid phases, wherein the arch-shaped shade part is the section area occupied by the liquid phase.

FIG. 3A-FIG. 3B is a scheme for showing the experimental device of the invention, in which FIG. 3A and FIG. 3B show two possible working positions of the gamma ray emitter and the gamma ray detector.

Figure 1:
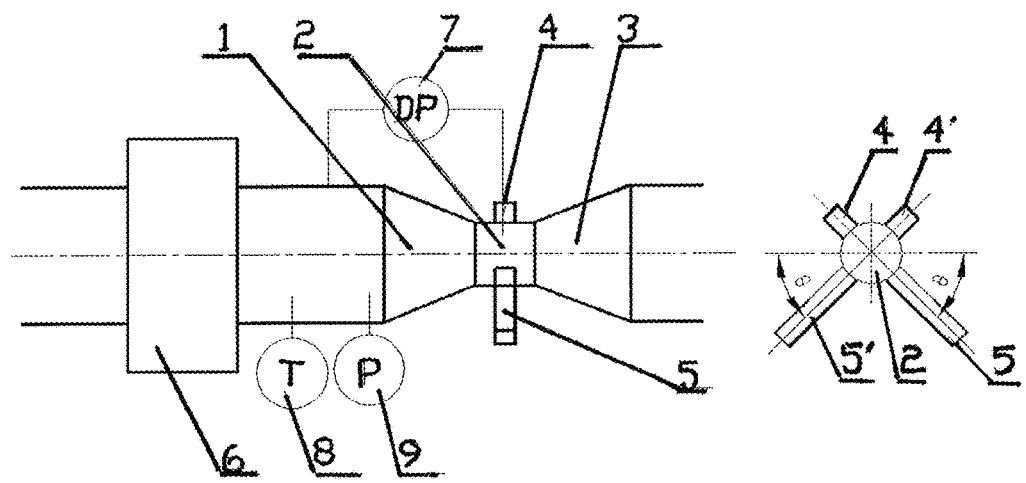
FIG. 1 is a scheme for showing the device of the invention, in which individual drawing reference signs have the following meanings: 1. Inlet pipesection of the Venturi tube; 2. Throat pipesection of the Venturi tube; 3. Outlet pipesection of the Venturi tube; 4 and 4'. Gamma ray emitter; 5 and 5'. Gamma ray detectors; 6. Apparatus for metering the total volume flowrate; 7. Component for measuring the differential pressure; 8. Component for measuring temperature; 9. Component for measuring pressure. Wherein the right drawing is the sectional view of the throat pipesection in the left drawing; the positions signed by the drawing references 4 and 4' and 5 and 5' only illustratively show two possible positions of the gamma ray emitter and the gamma ray detector, and in fact, only one set of the gamma ray emitter and gamma ray detector can satisfy measurement requirements.

The above drawings are provided merely for illustrating the technical concept and technical solution of the invention, and they are not intended to limit the present invention in any attempts.

DETAILED DESCRIPTION OF THE INVENTION

In order to facilitate the understandings to the invention, some terms used in the field of the multiphase metering are simply described as follows:

The term "multiphase flow" is meant to a mixed fluid consisting of a gas phase and a liquid phase, wherein the liquid phase can be classified into an oil phase and a water phase, and the oil phase and the water phase either may be miscible with each other to form a single liquid phase, or can be immiscible with each other, being two liquid phase independently from each other.

The term "wet gas" is meant to a specific multiphase flow, in which the oil phase and the aqueous phase are deemed as a single liquid phase. That is, the wet gas is a multiphase flow essentially consisting of a gas phase and a liquid phase, wherein the gas-phase volume is greater than 90%, preferably greater than 95%, and more preferably greater than 98% of the total volume of the multiple phase.

The term "volume flowrate" is meant to the volume of a fluid which flows through a certain section in unit time, and in the system of units (SI), its dimension may be $m^3/s$. According to different temperature and pressure at which the fluid is, the volume flowrate can be classified into the working volume flowrate and the standard volume flowrate, wherein the former is the volume flowrate actually measured at actual temperature and pressure of the working conditions, and the latter is obtained by converting the former into the volume flowrate under standard situations (298 K, 101.325 kPa) via the PVT calculation.

The term "phase fraction" is meant to the percentages of individual phases in a multiphase fluid. According to the calculation basis, the phase fraction can be classified into the linear phase fraction, the area phase fraction and the volume phase fraction. The linear phase fraction refers to the ratios of respective absorption route length of gas phase and liquid phase based on the total absorption route length of the gas phase and liquid phase along a line, e.g., along the transmission direction of gamma rays, called as the gas linear phase fraction $\alpha_g$ and the liquid linear phase fraction $\alpha_l$, respectively, in which, the subscript g denotes gas, and the subscript l denotes liquid. The area phase fraction refers to, at a certain cross section, the percentage of the area occupied by gas phase or liquid phase based on the total area of the cross section, called as the gas area fraction $\alpha_g$ and the liquid area fraction $\alpha_l$, respectively. The volume phase fraction refers to the percentage of respective volume flowrate of gas and liquid phases based on the total volume flowrate of the multiphase fluid. All the phase fractions, no matter the linear phase fraction, the area phase fraction, and the volume phase fraction, are percentages without dimension, and they can meet the following condition: $\alpha_g+\alpha_l=1$ or $\alpha_g+\alpha_o+\alpha_w=1$. For clarity, when the term "phase fraction" is mentioned, the inventor will specially notes that whether it is a linear phase fraction or an area phase fraction.

The term "gas content" is meant to the volume phase fraction of gas phase, represented by GVF; the term "liquid content" is meant to the volume fraction phase of liquid phase, represented by LVF; obviously, in the case of wet gas, GVF+LVF=1.

The term "radial direction" is meant to the diameter direction of a round.

The term "vertical" is meant to the same direction as the direction of the gravity accelerated velocity or counter direction thereof.

The term "horizontal" is meant to the direction that is perpendicular to the direction of the gravity accelerated velocity.

The term "slip difference" refers to the difference between gas velocity and liquid velocity of a gas and liquid mixed fluid in the same one pipeline, so the unit of slip difference is the unit of velocity. The term "gas and liquid slip factor" refers to the gas velocity to liquid velocity ratio of the gas and liquid mixed fluid in the same one pipeline, dimensionless. There are a plurality of factors which can result in the slip difference, mainly for the reason that gas phase and liquid phase are different from each other markedly in the density, viscosity, compressibility and other properties. In actual pipeline, because gas phase has a relatively low density and viscosity, the velocity of gas phase is often higher than that of liquid phase, thereby to produce the slip difference. Errors in the measurement of gas-phase flowrate and liquid-phase flowrate in a wet gas can be caused due to the presence of the slip difference phenomenon.

The term "stable-state flow" refers to that the flowing pattern of a fluid is not changed with time in macroscopic view, that is, the fluid reaches a so-called "stable state".

The following text makes descriptions in detail to the device and method for the online measurement of gas-phase flowrate and liquid-phase flowrate of wet gas in a horizontal pipe.

The first aspect of the invention relates to a device for the online measurement of gas flowrate and liquid flowrate of wet gas in a horizontal pipe, comprising the following parts: a horizontal Venturi tube and a gamma ray monitor. The following text will give some introductions to the two parts, respectively.

Horizontal Venturi Tube

Venturi tube is a common device in the flowrate metering field, and it can act the function of "throttling". The essential components of the Venturi tube includes a truncated cone-shaped inlet pipesection with section area reduced gradually, a cylindrical throat pipesection and a truncated cone-shaped outlet pipesection with section area increased gradually. A fluid flows into the truncated cone-shaped inlet pipesection with section area reduced gradually of the Venturi tube from upstream pipeline, and with the gradual reduction of the area of the fluid, the "throttling" action occurs, that is, the flow velocity of the fluid is increased while the static pressure is reduced. When the fluid reaches the cylindrical throat pipesection of the Venturi tube which has a minimum area, the flow velocity is maximum, and the static pressure is lowered to be minimum. Then, the fluid flows out of the venturi tube through the truncated cone-shaped outlet pipesection with section area increased gradually to enter downstream pipeline. The pressure difference $\Delta P$ can be calculated by measuring the pressure P1 at the upstream pipeline or at the juncture of the upstream pipeline with the inlet pipesection of the venturi tube and measuring the pressure P2 at the throat pipesection of the venture tube, and then by combining the structural parameters of the venturi tube, the flowrate or flow velocity of the fluid can be calculated. As to more specific structures of the venturi tube and more equations for calculating the flowrate or flow velocity of the fluid, please see any hydrodynamics textbook. In the invention, the venturi tube is required to be arranged horizontally, that is, the central axis of the venturi tube exhibits a horizontal direction.

Gamma Ray Monitor

The gamma ray monitor is a commonly-used monitor in the field of the multiphase flowrate metering, generally comprising a gamma ray emitter and a gamma ray detector. In the invention, the gamma ray emitter and the gamma ray detector are required to be arranged in a manner that gamma rays emitted by the gamma ray emitter can radially penetrate through the cross section of the throat pipesection to reach the gamma ray detector. The gamma ray monitor has the following working mechanism: radioactive source in the gamma ray emitter arranged on a side of the pipe can emit gamma rays having a certain initial intensity, i.e., the emissive intensity $N_0$, preferably calibrated gamma rays. When the gamma rays transmit an absorption medium, the intensity attenuation can occur due to the interactions with the absorption medium, e.g., photoelectric effect, Compton scattering, and the production of electron pairs, that is, the absorption medium absorbs at least a portion of the gamma rays. Then, the gamma ray detector arranged on another side of the pipe may detect the intensity of the attenuated gamma rays, i.e., the transmission intensity N. Based on some equations, the absorption coefficient of the absorption medium can be calculated. Various suitable radioactive sources can be used as the radioactive source used in the invention. In the case of a multiphase fluid as the absorption medium, since the gas phase and the liquid phase have different absorption coefficients to gamma rays, for multiphase fluids having different ratios of gas and liquid phases, they have different absorption coefficients. Respective absorption coefficients of the gas and liquid phases can be beforehand obtained as important constants in the measurement of the present invention by respectively measuring the gas and liquid phases separated by using a conventional liquid and gas separation device (e.g., a cyclone separator or a condensing separator). On this basis, it is possible that information regarding to the phase fractions of individual phases may be provided by making analyses and calculations to the measured absorption coefficients of the gas and liquid mixture.

The gamma ray monitor used in the invention is well known, and as for more working mechanisms and more details of the monitor, relevant monographs may be referred to.

The invention requires the gamma ray emitter and the gamma ray detector to be arranged in a manner that gamma rays emitted by the gamma ray emitter can radially penetrate through the cross section of the throat pipesection to reach the gamma ray detector. The radial arrangement is also required to let gamma ray must pass through the gas and liquid phases. A radial arrangement which can certainly pass through the gas and liquid phases is the vertical radial arrangement, because even if wet gas contains very less liquid phase, after the sedimentation of the liquid phase occurs, there will be some liquid at the bottom of the horizontal pipe. However, a person skilled in the art, according to specific situations, also can select a non-vertical radial direction, i.e., a declining radial direction, and the angle θ ($0°≤θ≤90°$) between the declining radial direction and the horizontal direction is used to show the specific orientation of the declining radial direction. A person skilled in the art can easily select the specific orientation of the declining radical direction by making simple estimations to history experiential values of the gas content of wet gas so that gamma rays still can be assured to pass through the gas and liquid phase along the declining radial direction. In practice, a person skilled in the art can select the specific direction of the declining radial direction by the means of a simple trial-and-error method for the reason that once the gamma rays only can pass through the gas phase, the reading the gamma ray detector will rapidly decrease to a next order of magnitude, and when such situation is excluded upon measurement, the gamma rays can be assured to pass through the gas and liquid phases. In addition, in one embodiment of the invention, the gamma ray monitor may make measurements in a fixed radial direction or a variable radial direction. The vertical radial direction is preferred. However, any declining radial direction also can be used, for example, the angle between said radial direction and the horizontal radial direction may be one selected from the group of: $θ≥10°$, $θ≥15°$, $θ≥30°$, $θ≥45°$, $θ≥60°$, $θ≥75°$, $θ≥80°$, $θ≥85°$, or $θ=90°$. As long as the gamma ray can be assured to pass through the gas and liquid phases, measuring results obtained by using individual angles can be comparative to each other in the aspect of measuring error. As described in the following text, due to the above fact, the gamma ray monitor can be flexibly arranged in any angle according to specific on-the-spot spatial conditions of oil and gas transferring pipeline, while the measurement precision will not be influenced.

Further, the gas and liquid flowrate metering device of the invention may optionally comprises a total volume flowrate metering device located upstream or downstream of the horizontal venturi tube for measuring the total volume flowrate of the multiphase fluid. The total volume flowrate metering device can be used to measure the total volume flowrate, and any flowrate meters suitable for metering the total volume flowrate of a fluid as known in the art of the flowrate metering may be used, for example, but not limited to, e.g., an elbow flowrate meter, a venturi flowrate meter, a ratometer, a float flowrate meter, and an orifice flowrate meter. As for the working mechanism and apparatus details of the total volume flowrate metering device, skilled man can refer to relevant textbooks or product specifications of manufacturers of the device. Alternatively, the total volume flowrate metering device also may be a flow velocity metering device, and the flow velocity metering device can measure the average flow velocity of the multiphase fluid which then is multiplied by the cross section area of the pipe to give the total volume flowrate. An exemplary flow velocity metering device may be a device for measuring the flow velocity by the "cross-correlation method" in the art. The basic theory of the method is that two sensors are arranged at the two points which are away from each other in a known distance along the flowing direction of the fluid, and the sensors may be sensors based on microwave, ray, differential pressure or electrical impedance which can be used to measure the density, electrical conductivity or inductance of the fluid. In work, the two sensors measures the time required by the same one signal passing through such known distance, and then the average velocity of the fluid is calculated. The theory of the "cross-correlation method" and the calculation formulae used thereby are known in the prior art, for example, referring to HANDBOOK OF MULTIPHASE FLOWRATE METERING (published by Norway oil and Gas Measurement Association, 2005.03, 2nd Edition).

However, preferably, the multiphase flowrate metering device of the invention does not use a single total volume flowrate metering device located upstream or downstream of the horizontal venturi tube for measuring the total volume flowrate of the multiphase fluid, but the horizontal venturi tube according to the invention for the measurement of the total volume flowrate. That is, the multiphase fluid flowrate metering device of the invention may further comprise a differential pressure measuring component for measuring the pressure difference between the upstream and the throat of the venturi tube, a pressure measuring component for measuring the pressure of wet gas at the upstream of the venturi tube and a temperature measuring component for measuring the temperature of wet gas. Hence, according to the mechanisms of a conventional venturi tube for measuring flowrate, the horizontal venturi tube is used to accomplish the measurement of the total volume flowrate, while it is unnecessary to use a single total volume flowrate metering device.

The second aspect of the invention relates to a method for the online measurement of gas flowrate and liquid flowrate of a wet gas in a horizontal pipe, and the concrete steps are described in the "Summary of the invention" portion. The following contents describe each step more particularly.

In the step a, wet gas passes through a segment of a horizontal ventui tube. At the throat pipesection of the horizontal venturi tube, the liquid and gas phases in the wet gas are at least partially stratified under the action of the gravity force, and thus the liquid-gas stratification phenomenon occurs at the throat of the horizontal venturi tube. Furthermore, at least partial liquid-gas stratification phenomenon may easily occur in a horizontal pipeline, even inevitably. For example, there is the at least partial stratification phenomenon in the horizontal pipelines at the upstream and downstream of the horizontal venturi tube. The gas-liquid interface produced after the at least partial gas-liquid stratification either can be a clear interface or a vague interface, which depends on whether or not the stratification is complete and the turbulent degree of fluid. The inventor of the present application, after long-period experiments, finds out that the gas-liquid stratification at the throat of the horizontal venturi tube is more valuable than the gas-liquid stratification in the horizontal pipelines at the upstream and downstream of the venturi tube, that is, it can be used in the measurement of the flowrates of the gas and liquid phases.

In the step b, the radial linear phase fraction $\alpha_{g\text{-}\theta}$ of the gas phase along the cross section of the throat pipesection is measured by a gamma ray monitor, wherein the gamma ray monitor comprises a gamma ray emitter and a gamma ray detector, and the gamma rays emitted by the gamma ray emitter can radially pass through the gas and liquid phases to reach the gamma ray detector. The arrangement of the gamma ray monitor is described as those for describing the first aspect of the invention. Any radial direction can be used, as long as gamma rays can be assured to pass through the gas and liquid phases.

In the step c, gas phase flowrate $Q_g$ and liquid phase flowrate $Q_l$ are calculated with the total volume flowrate $Q_t$ and the above radial linear phase fractions $\alpha_{g\text{-}\theta}$ of the gas phase in accordance with an equal-diameter eccentric round model, and as for specific equations, the following text will make descriptions in detail. As to the total volume flowrate metering device, when it is used, the selection to the type of the total volume flowrate metering device and the arrangement thereof are described as those for describing the first aspect of the invention. Now, we will put emphasizes to the introduction of "equal-diameter eccentric round model", and just because the applicant originally uses the model, the online measurement of gas flowrate and liquid flowrate of wet gas in a horizontal pipe becomes possible and feasible in technique.

Figure 2A:
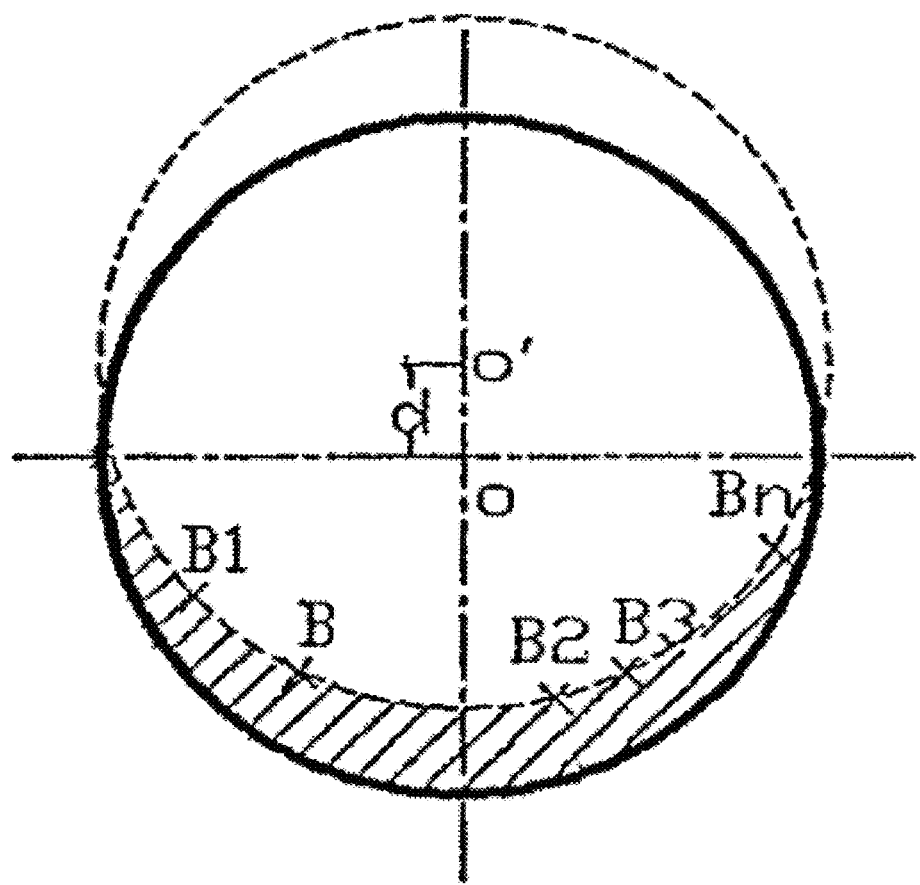
FIG. 2A-FIG. 2C is a scheme for showing the equal-diameter eccentric round model of the invention, in which the round as plotted with the solid line in FIG. 2A denotes the cross section of the horizontal Venturi tube; the round as plotted by the dotted line denotes the equal-diameter eccentric round; the arc line B1-B1-B3- . . . -Bn denotes the profile of the gas and liquid phase interface; the shade part is the section area occupied by the liquid phase.
Figure 2B:
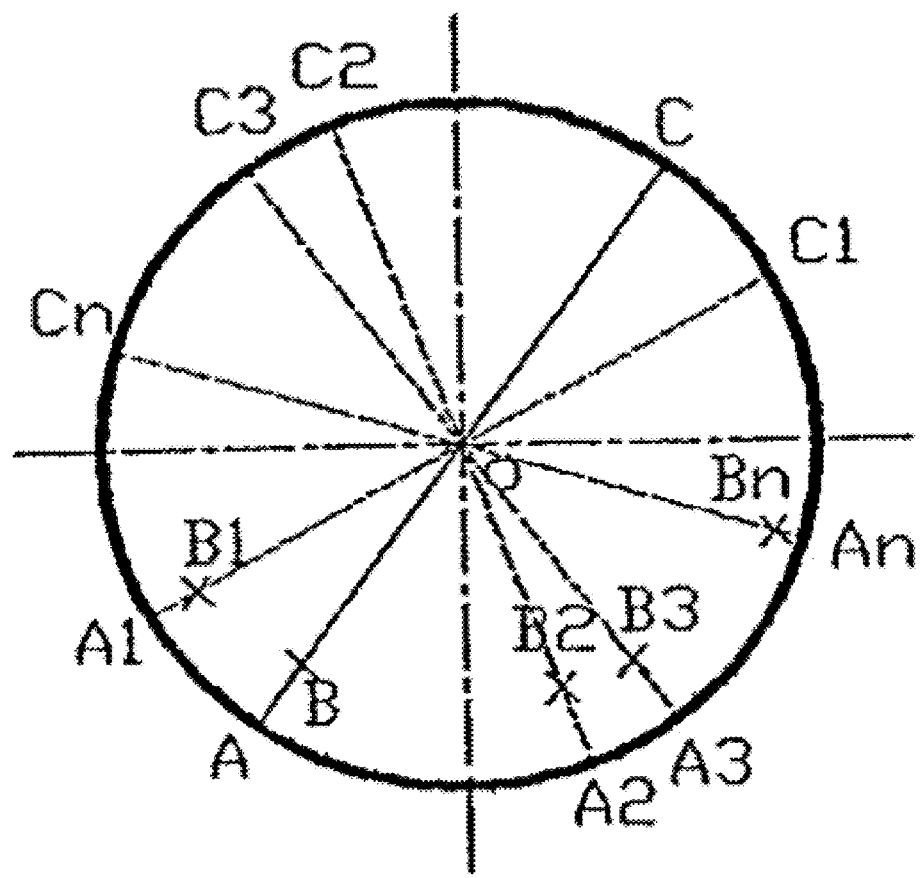

The so-called "equal-diameter eccentric round model" is meant to a model based on the hypothesis that after the complete stratification of the gas and liquid phases occurs in the horizontal circular pipeline due to the sedimentation of the liquid phase, the area in which the liquid phase is present is such an area: after a round which initially completely overlaps with the circular cross section of the horizontal pipeline (the circular cross section of the horizontal pipeline can be called as "section round") shifts upward a distance d along the vertical radial direction (d is called as eccentric distance), a "equal-diameter eccentric round" can be obtained, and the falcate area in the "section round" which does not overlap with the "equal-diameter eccentric round" just is the area occupied by the liquid phase when the liquid and gas phases are assumed to be completely stratified. Other area in the circular pipeline is the area occupied by the gas phase. As shown in FIG. 2A, the round 0 is the section round, and the round 0' is the eccentric round; the falcate shape area is assumed to be the area occupied by the liquid phase after the gas and liquid phases are completely stratified, and other area in the pipeline is deemed as the area occupied by the gas phase. The boundary line of the two areas is deemed as the gas-liquid interface. In the case of the equal-diameter eccentric round model, the gas-liquid interface is a clear interface which can bring conveniences to the calculations of the gas and liquid flowrates in accordance with the invention. It is worthy to be pointed out that an actual gas and liquid phase interface is not such a clear interface, while it may be a vague interface, in particularly, in the case of the incomplete stratification of the gas and liquid phases. Furthermore, even if the gas and liquid phases are completely stratified, a corresponding actual gas-liquid interface only may be an interface which is close to the above clear interface, and it is difficult for the actual interface to completely reache the above clear interface. However, in the present invention, no matter how actual situations of the gas-liquid interface are, nominal gas-liquid interface points of the liquid and gas phases can be calculated starting from the gas linear phase fraction $\alpha_{g\text{-}\theta}$ with a nominalization method. By combining the contents as shown in FIG. 2B, the nominalization method are introduced as follows: at a certain radial direction, the ratio of the length of the gas phase through which gamma rays pass to the diameter of the section round is the gas linear phase fraction $\alpha_{g\text{-}\theta}$. For example, as shown in FIG. 2B, when gamma rays pass through along the diameter AC, it is deemed that the line segment BC represents the length of the gas phase through which the gamma rays pass; the line segment AB represents the length of the liquid phase through which the gamma rays pass; and AC represents the diameter of the section round. Thus, according to the definitions for the gas linear phase fraction $\alpha_{g\text{-}\theta}$, the $\alpha_{g\text{-}\theta}$=BC/AC=BC/2R can be seen. When the $\alpha_{g\text{-}\theta}$ is measured by using a gamma ray monitor, the BC length can be calculated by using the equation: BC=2R×$\alpha_{g\text{-}\theta}$ to further determine the B point position. Thus, it can be deemed that the B point just is the gas-liquid interface point after the nominalization along the diameter AC direction, also called as the nominal gas-liquid interface point. It should be noted that the gas-liquid interface point is called as the "nominal" gas-liquid interface point for the reason that it is only the gas-liquid interface point assumed during the nominalization calculation, but not necessarily a true gas-liquid interface point. The diameter direction is varied, for example, the diameters A1C1, A2C2, A3C3, . . . , AnCn, to measure a series of $\alpha_{g\text{-}\theta}$, and thus a series of gas-liquid interface points B1, B2, B3, . . . , Bn can be calculated by using the above nominalization method. Then, these points B, B2, B3, . . . , Bn are connected to give a nominalized gas-liquid interface for subsequent calculations. Hence, in another word, the "equal-diameter eccentric round model" also can be described as follows: at any radial direction that penetrates the gas and liquid phases in the horizontal circular pipeline, it can be deemed that the length of the gas phase is equal to 2R×$\alpha_{g\text{-}\theta}$ and the length of the liquid phase is equal to 2R×(1−$\alpha_{g\text{-}\theta}$), and according to the lengths, the positions of the calculated gas-liquid interface points are the positions of the nominal gas-liquid interface points. All the positions of the nominal gas-liquid interface points are connected to give the nominal gas-liquid interface. The nominal gas-liquid interface may be represented by the segment of curve of the above equal-diameter eccentric round which still remains in the section round, and thus the above process for determining the nominal gas-liquid interface is called as the "equal-diameter eccentric round model".

Although the proviso for establishing the equal-diameter eccentric round model is the complete stratification of the gas and liquid phases, the applicant has surprisingly found out in practice that even if the gas phase and the liquid phase is incompletely stratified, but partially stratified, when making calculations and measurements according to the above "equal-diameter eccentric round circle", a measurement precision which is the same as that of the completely stratification of the gas and liquid phases can be still obtained. In another word, when making measurements and calculations according to the model in practice, whether or not the gas phase and the liquid phase is completely stratified, it will not influence the precisions of the measuring and calculating results. Such a surprising finding can have very huge guiding significants to the measuring practices: I. in the measuring practice, the judgement for whether or not gas phase and liquid phase are completely stratified can be completely omitted, further to omit physical apparatus in the measuring device for assuring the completely stratification of the gas and liquid phases; II. Based on the finding, the precision measurements of the gas and liquid flowrates of wet gas in a horizontal pipe may be possibly accomplished, because the wet gas is not required to be present in a form of homogenous mist fluid, that is, whether or not gas phase and liquid phase are stratified and whether or not the stratification is complete, both of them cannot interface the measurements of the flowrates of the gas and liquid phases. Due to above features, the measurement of the wet gas flowrate which only can be carried out in a vertical pipeline also can be carried out in a horizontal pipeline.

Figure 2C:
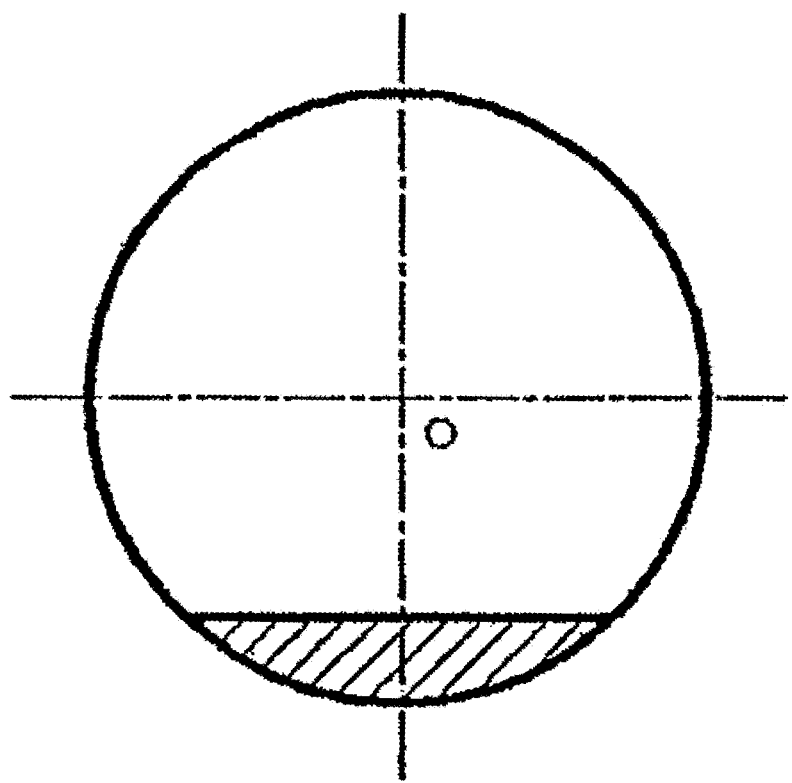

The above "equal-diameter eccentric round model" also far way goes beyond the expectation of a person skilled in the art for the reason that conventionally, based on the levelling property of a liquid, a person skilled in the art can considers that after the complete stratification of gas phase and liquid phase in a circular pipeline, the interface between the gas phase and the liquid phase is a horizontal straight line. That is, the area as occupied by the liquid phase is arch-shaped in geometry, as shown in FIG. 2C. Thus, a person skilled in the art cannot envisage that the gas-liquid interface may be described with the above "equal-diameter eccentric round model".

After the equal-diameter eccentric round model is inventively established, in measuring practices, the volume flowrate of the gas and liquid phases can be calculated starting from the linear $\alpha_{g-\theta}$ data measured along any radial direction at the throat of the horizontal venturi tube according to the equal-diameter eccentric round model, while it is not necessary to make the calculation starting from the linear $\alpha_{g-\theta}$ data measured along the vertical radial direction. Thus, the feature can provide flexibility to the arrangement angel of the gamma ray monitor, and it can provide more conveniences when using the flowrate metering device in a petroleum platform in sea having a limited space or making modification arrangement of a flowrate meter in existing wet gas pipelines.

Gas phase flowrate $Q_g$ and liquid phase flowrate $Q_l$ can be calculated with the total volume flowrate $Q_t$ and the above radial linear phase fractions $\alpha_{g-\theta}$ of the gas phase in accordance with an equal-diameter eccentric round model with the following specific equations:

Calculation of the eccentric distance d:

$$d = (R - 2R\alpha_{g\_\theta})\sin\theta + \sqrt{R^2 - (R - 2R\alpha_{g\_\theta})^2 \cos^2\theta}$$

wherein R denotes the radius of the throat pipesection, and $\theta$ denotes the angle of the radial direction used during the measurement relative to the horizontal radial direction;

Calculation the area phase fraction $\alpha_{sg}$ of the gas phase:

$$\alpha_{sg} = \frac{4R^2 \cos^{-1}\left(\frac{d}{2R}\right) - \sqrt{(4R^2 - d^2)d^2}}{2\pi R^2};$$

Calculation of the volume phase fraction GVF of the gas phase:

$$GVF = \frac{\alpha_{sg} \times S}{\alpha_{sg} \times S + 1 - \alpha_{sg}}$$

wherein S denotes the slip factor between the gas phase and liquid phase; when the slip difference is taken into account, S is calculated by using experimental equations; when the slip difference is not taken into account, S=1, so GVF=$\alpha_{sg}$;

Calculation of the gas and liquid flowrates of the wet gas in the horizontal pipe:

$Q_g = Q_t \times GVF$ $Q_l = Q_t \times (1 - GVF)$

The total volume flowrate $Q_t$ may be measured by a total volume flowrate metering device located at the upstream or downstream of the horizontal venturi tube. Alternatively, the total volume flowrate also can be calculated with the pressure difference between the upstream and the throat of the venturi tube measured by the differential pressure measuring component, the wet gas pressure measured by the pressure measuring component, and the wet gas temperature measured by the temperature measuring component (these components are described in the first aspect of the invention) according to the following conventional calculation equations of venturi tube:

$$Q_t = C \cdot \frac{\pi d^2}{4} \cdot \frac{1}{\sqrt{1 - \beta^4}} \cdot \sqrt{2 \cdot (\Delta P / \rho_{mix})}, \text{m}^3/\text{s}$$

Wherein C denotes the efflux coefficient of the flow, dimensionless; d denotes the inner diameter of the throat pipesection of the Venturi tube; $\beta$ denotes the ratio of the inner diameter of the throat pipesection of the Venturi tube to the inner diameter of the pipe at the inlet; $\Delta P$ denotes the pressure difference measured by the differential pressure measuring component; $\rho_{mix}$ is the mixed density of the wet gas. As to the unit of individual physical parameters, if necessary, each of them uses international units.

The calculations of the slip factor may be based any model which has been reported in documents, and some model for options are as follows:

(1) Momentum Flux Model $$S = \left(\frac{\rho_g}{\rho_l}\right)^{0.5}$$

wherein $\rho_g$ denotes the density of the gas phase, and $\rho_l$ denotes the density of the liquid phase.

As for more details of the model, please see the contents in the document: J. R. Thome "Void Fraction in Two-Phase Flows", Engineering Data Book III (Wolverine Tube Inc.), Chapter 17, 2004.

(2) Smith Model $$S = \varepsilon + (1-\varepsilon)\left[\frac{\left(\frac{\rho_l}{\rho_g}\right) + \varepsilon\left(\frac{1-x}{x}\right)}{1 + \varepsilon\left(\frac{1-x}{x}\right)}\right]^{0.5}$$

wherein $\rho_g$ denotes the density of the gas phase; $\rho_l$ denotes the density of the liquid phase; $\varepsilon$ denotes the entrainment factor; and x denotes the dryness.

As for more details of the model, please see the contents in the document: S. L. Smith, Void Fractions in Two-Phase Flow: A Correlatioin Based Upon an Equal Velocity Head Model, Proceedings of the institution of mechanical Engineers, Vol. 184, No. 36, pp 647-664, 1969.

(3) Chisholm Model $$S = \left[1 - x\left(1 - \frac{\rho_g}{\rho_l}\right)\right]^{0.5}$$

Wherein $\rho_g$ denotes the density of the gas phase; $\rho_l$ denotes the density of the liquid phase; and x denotes the dryness.

As for more details of the model, please see the contents in the document: D. Chisholm, Pressure Gradients due to Friction During the Evaporating Two-Phase Mixtures in Smooth Tubes and Pipesections, Heat Mass Transfer, Vol. 16, pp 347-358, 1973. Pergamon Press.

(4) Haimo Model $$S = \frac{(1-\alpha_{sg})\left(\frac{1}{\mu'_k}\frac{\alpha_{sg}}{1-\varepsilon} - 2\left(\frac{\alpha_{sg}}{1-\varepsilon} - 1\right)\right)}{\left(1 - \frac{\alpha_{sg}}{1-\varepsilon}\right)^2 + \varepsilon\left(\frac{1}{\mu'_k}\left(\frac{\alpha_{sg}}{1-\varepsilon}\right)^2 - 2\left(\left(\frac{\alpha_{sg}}{1-\varepsilon}\right)^2 - \frac{\alpha_{sg}}{1-\varepsilon}\right)\right)}$$

wherein $\alpha_{sg}$ denotes the area phase fraction of the gas phase, $\mu'_k = (1-\varepsilon)\mu_k + \varepsilon$; $\mu_k$ denotes the ratio of the viscosity of the gas to viscosity of liquid phases, and $\varepsilon$ denotes the entrainment factor which can obtained according to experience, or can be obtained by the following method: the device of the invention is used to measure the gas flowrate and liquid flowrate of the same one wet gas together with a standard gas flowrate metering device and a standard liquid flowrate metering device, and after limited experiments, a set of the experimental values of gas flowrate and liquid flowrate and a set of the true values of gas flowrate and liquid flowrate are respectively obtained. Following this, the experimental data is subject to the data regression to give the experimental value of the entrainment factor, and further to apply the regressed experimental value of the entrainment factor as a known constant in occasions wherein the measuring device of the invention is used alone. The data regression technique is well known for a person skilled in the art.

The Haimo model is a model obtained by the applicant based on the modelling technology according to a large quantity of experimental data.

Embodiment

The following examples are provided for illustrating the technical solution of the invention, and they are only illustratively, but not limit the invention in any manner.

Verification experiments for the device and measuring method of the invention are carried out in English National Engineering Laboratory (abbreviated as NEL). The NEL is an authority for estimating and testing multiphase flow metering device which is well recognized in the world, and it is famous for its objective, authoritativity and strict. Thus, current mainstream gas-oil manufacturers require that multiphase flowrate meters provided by multiphase flowrate meter providers must pass through the tests in this laboratory. The measuring device of the invention is shown in FIG. 1, and individual components therein may be commercially available. FIG. 3 is a scheme for showing the experimental device set of the invention. At ambient temperature, the gas pump 10 is used to deliver a certain gas phase (e.g., air, nitrogen gas, natural gas or oilfield associated gas) which has been purified to a horizontal test pipeline via a standard gas flowrate metering system 11 (e.g., a speed-based flowrate meter for measuring the flowrate of gas), wherein the standard gas flowrate metering system 11 can measure the flowrate $Q_{gas}$ of the gas. At the same time, a liquid pump 12 delivers a certain liquid (e.g., crude oil, water or oil-water mixture) via a standard liquid flowrate metering system 13 (e.g., a volume flowrate meter for measuring the liquid flowrate) to horizontal wet gas pipelines, wherein the standard liquid flowrate metering system 13 can measure the flowrate $Q_{liquid}$ of the liquid phase. The above gas flowrate and liquid flowrate both are adjusted separately from each other, so that different conditions for measuring the wet gas can be established in the horizontal test pipeline, and the measurements are carried at under the different conditions for measuring the wet gas. The liquid and the gas may be mixed in the test pipeline to form the wet gas. The above wet gas may be measuring when it flows through the measuring device of the invention as shown by the dotted line in FIG. 3.

In the example, a single total volume flowrate metering device is not used, while the Venturi flowrate meter (as shown in FIG. 1) arranged on the horizontal test pipeline is used to measure the total flowrate $Q_t$ of the gas and liquid mixed flow by combining the measurements for the temperature, pressure of the wet gas and the pressure difference between the upstream and the throat of the Venturi tube. A gamma ray emitter 4 and a gamma ray detector 5 which are radially arranged at the two sides of the throat of the above horizontal Venturi tube are used to measure the linear phase fraction $\alpha_g$ of the gas phase. In individual example, the measurement directions of the gamma ray emitter 4 and the gamma ray detector 5 may be vertical radial direction or declining radial direction. The temperature meter 8 and the pressure meter 9 are respectively used to measure the temperature T and the pressure P of the above mixed flow before entering the horizontal Venturi tube. In experiment, the working pressure of the system is stabilized to 6 MPa, and the temperatures of the liquid and gas phases are stabilized to 80° C.

2. Determinations of True Values and Representation of Errors

The metering precisions of the standard gas flowrate metering system 11 and the standard liquid flowrate metering system 13 in the experiment are shown in Table 1:

TABLE 1

Standard flowrate metering systems of gas phase
and liquid phase and metering precisions thereof

| | Type | Precision |
|---|---|---|
| Standard liquid flowrate metering system | Turbine flowrate meter | ±0.2% |
| Standard gas flowrate metering system | Ultrasonic wave flowrate meter | ±0.3% |

The above $Q_{liquid}$ and $Q_{gas}$ values measured by the standard flowrate metering systems are deemed as the true values of the liquid and gas volume flows. The measuring values $Q_l$ and $Q_g$ obtained by various measuring methods are compared with the true values for making relevant evaluations. According to conventional means in the art, the error of the gas flow is expressed by a relative error: $E_g=(Q_g-Q_{gas})/Q_{gas}\times 100\%$; and the error of the liquid flow is expressed by a relative error: $E_l(Q_l-Q_{liquid})/Q_{liquid}\times 100\%$.

3. Measurements and Calculations of the Volume Flowrates of Gas Phase and Liquid Phase What physical parameters are directly measured by using the above measurement device is the total volume flowrate $Q_t$, the linear phase fraction $\alpha_{g-\theta}$ of the gas phase at the throat of the Venturi tube, and the temperature T and pressure P of the wet gas. As for a plurality of physical parameters of the gas, liquid and wet gas, e.g., viscosity, density, dryness and compressibility factor, they can be calculated by using any flow state equation according to the above T and P, and these calculations are conventional calculations in thermodynamics and hydrodynamics. Any thermodynamic textbook and any hydrodynamic textbook can be used for the references. The compositions of the gas and the liquid may be measured separately. In addition, during the calculations, if any specific physical size and geometrical features of the device of the invention are in need, they can be deemed to be well known because they can be easily measured in practice.

During the final calculations of the volume flowrates of gas and liquid phases, the following two calculation methods may be used:

3.1 The above-measured total volume flowrates $Q_t$ of the gas and liquid phases and the measured gas linear phase fraction $\alpha_{g-\theta}$ at the throat of the Venturi tube may be directly used to calculate the volume flowrates of the gas and liquid phases according to the following equations: $Q_g=Q_t\times\alpha_{g-\theta}$; $Q_l=Q_t\times(1-\alpha_{g-\theta})$. Then, the results of the volume flowrates of the gas and liquid phases are listed in columns H and I in Tables 2 and 3, and the relative errors of the results in relative to the true values are listed in columns L and M.

3.2 The calculation method of the invention is used to calculate the volume flowrates of the gas and liquid phases according to the above "equal-diameter eccentric round model" and "slip difference model". The corresponding results are respectively list in Columns J and K in Tables 2 and 3, and the relative errors of the results in relative to the true values are listed in columns N and O. the slip difference model employs the Haimo slip model.

4. Example 1

Figure 3A:
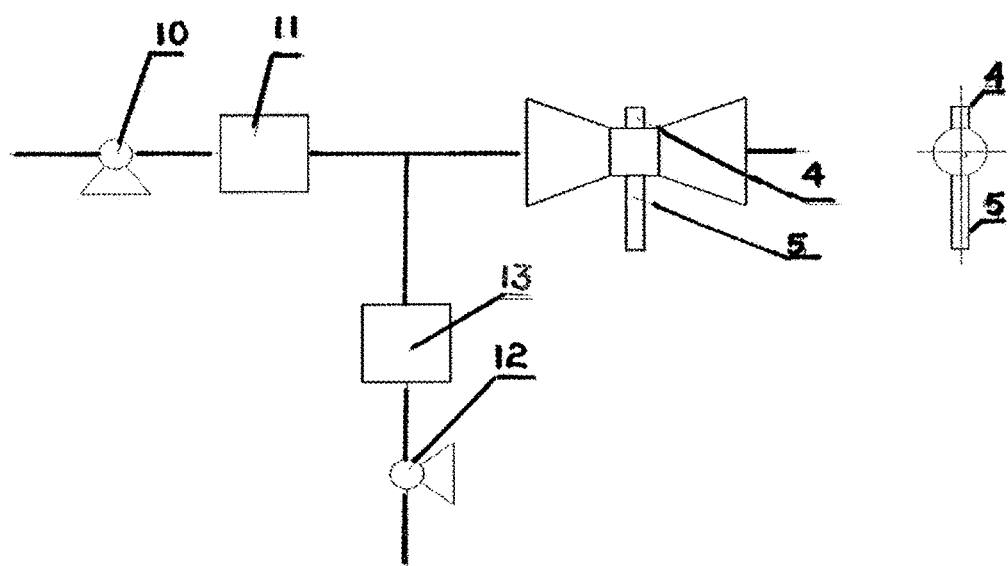

The device as shown in FIG. 3A is used, in which the measuring direction of the gamma ray monitor is vertical radial direction. Concrete measurement methods and concrete calculation method are described as above, and the measuring experimental data is listed in Table 2.

5. Example 2

Figure 3B:
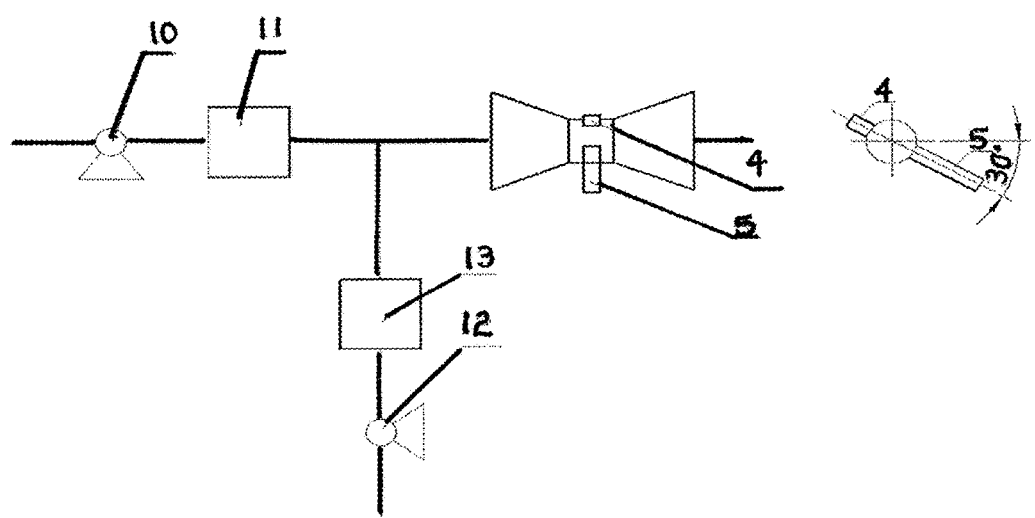

The device as shown in FIG. 3B is used, in which the measuring direction of the gamma ray monitor has an angle of 30° relative to the horizontal radial direction. Concrete measurement methods and concrete calculation method are described as above, and the measuring experimental data is listed in Table 3.

6. Relative Error of the Flowrates of Gas and Liquid Phases

Figure 4A:
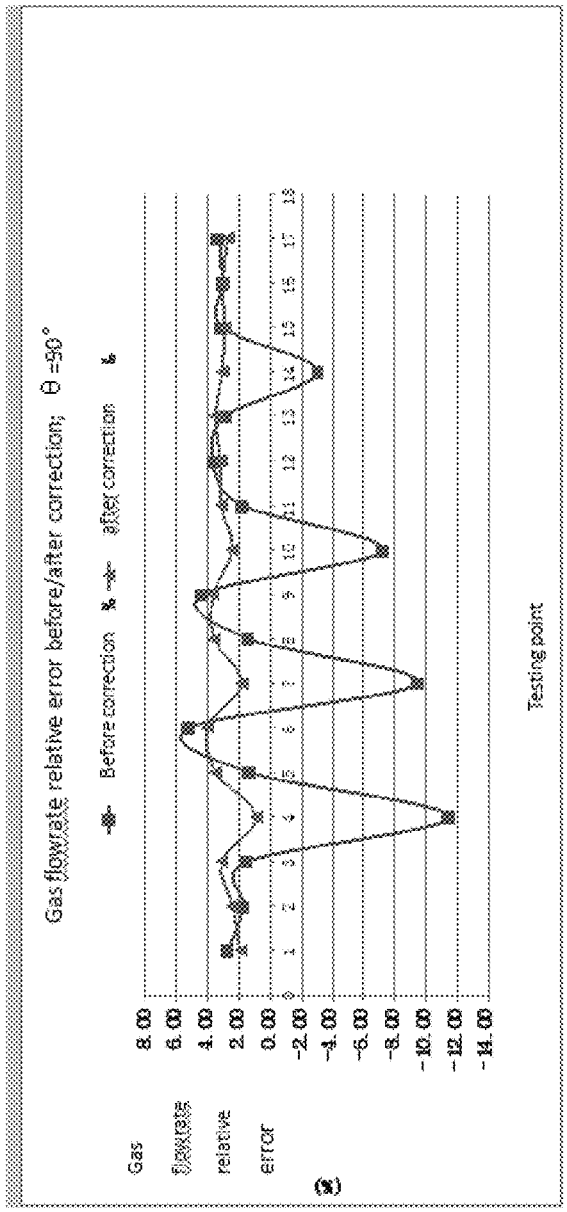
FIG. 4A-FIG. 4B shows the relative measurement error of the gas flowrate obtained by using the device and method of the invention.
Figure 4B:
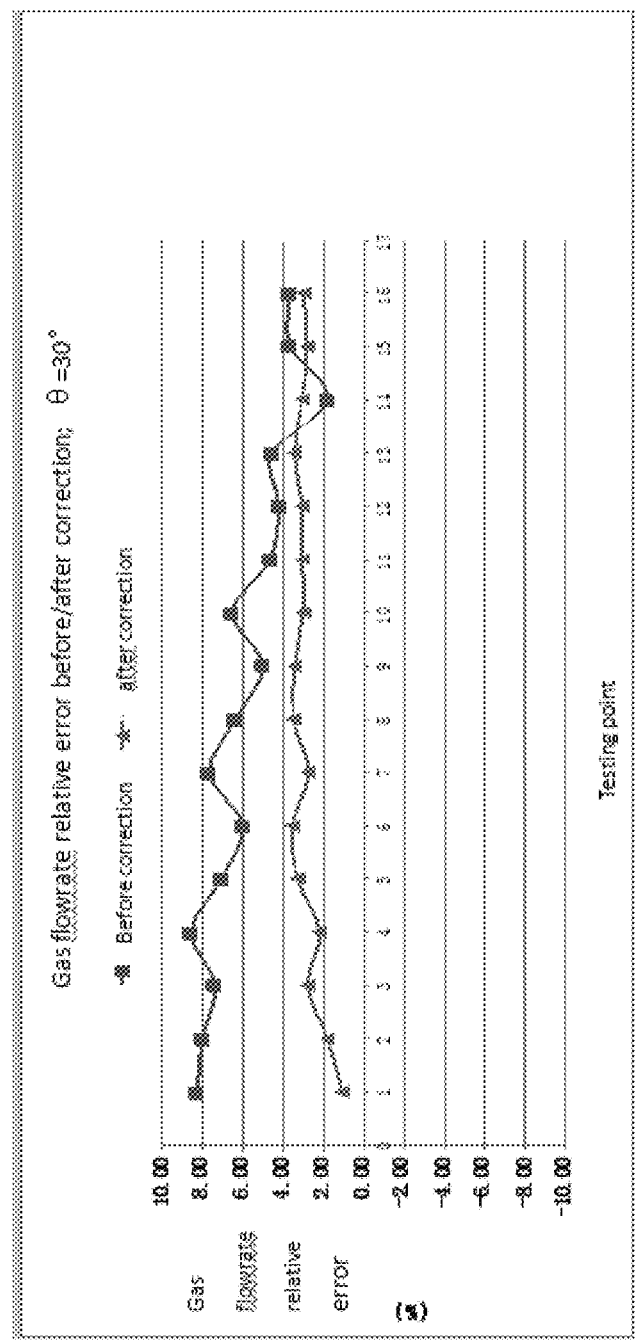
Figure 5A:
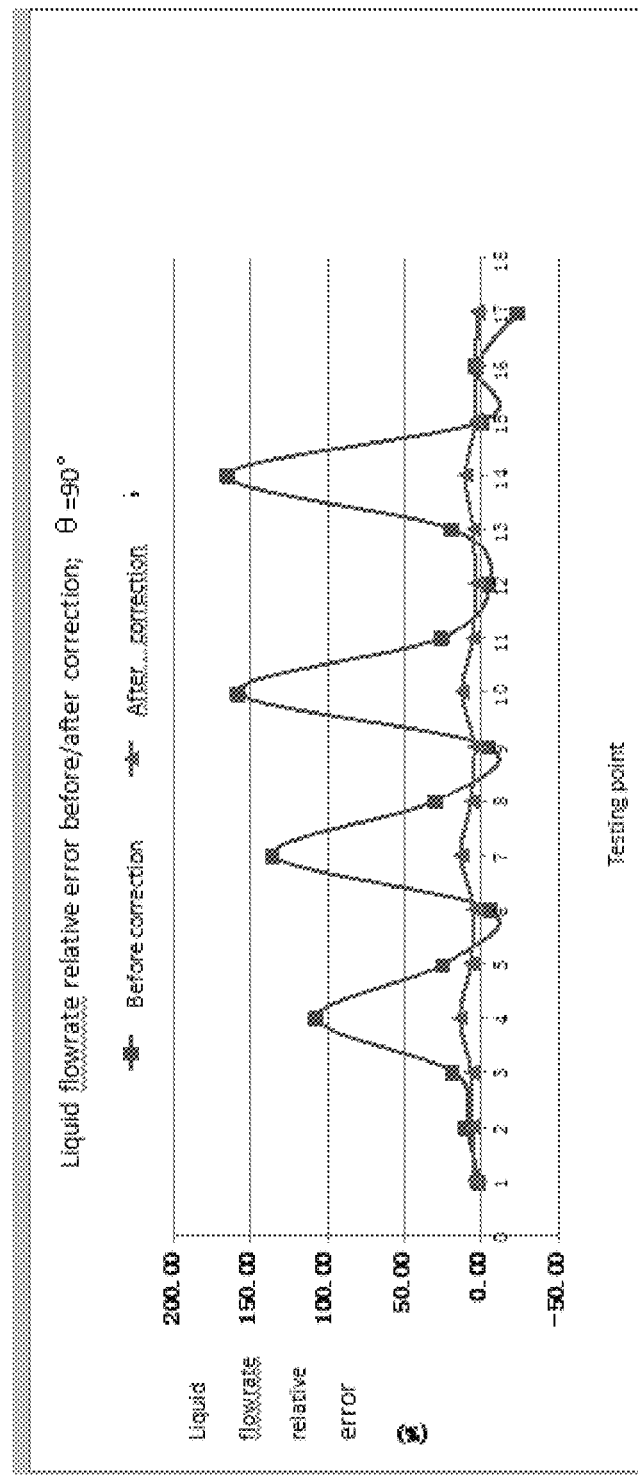
FIG. 5A-FIG. 5B shows the relative measurement error of the liquid flowrate obtained by using the device and method of the invention.
Figure 5B:
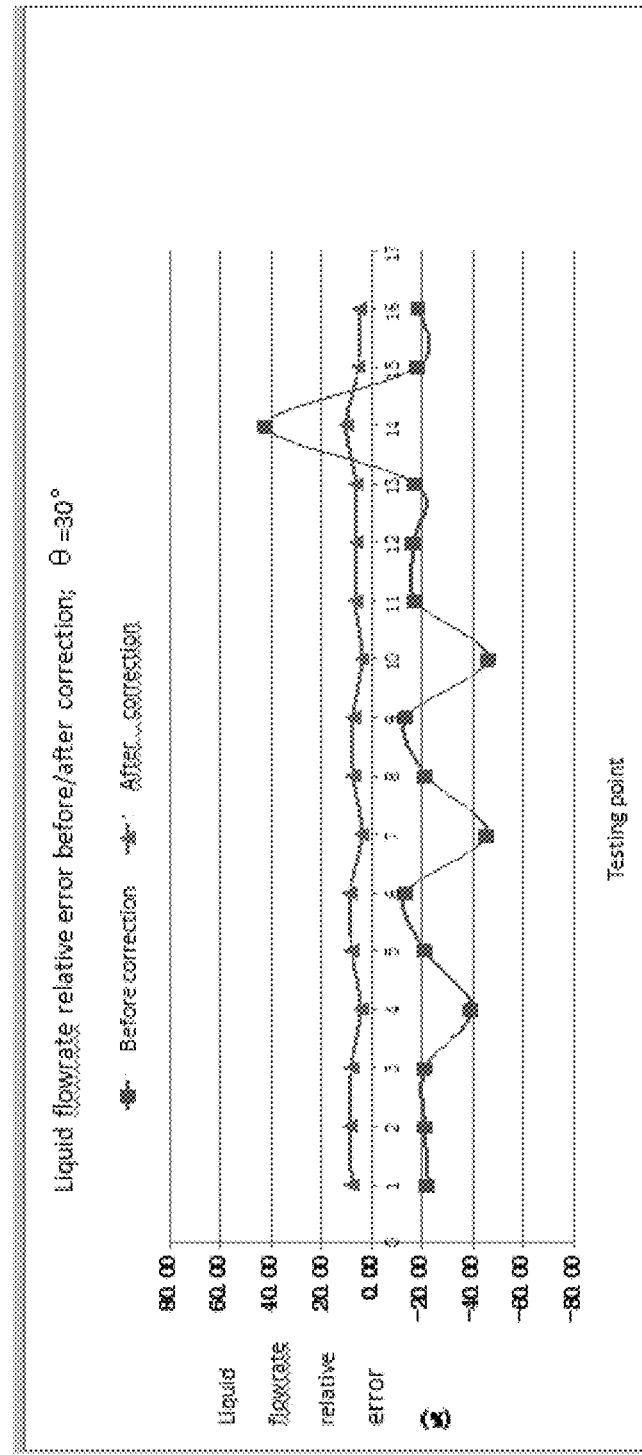
Figure 6:
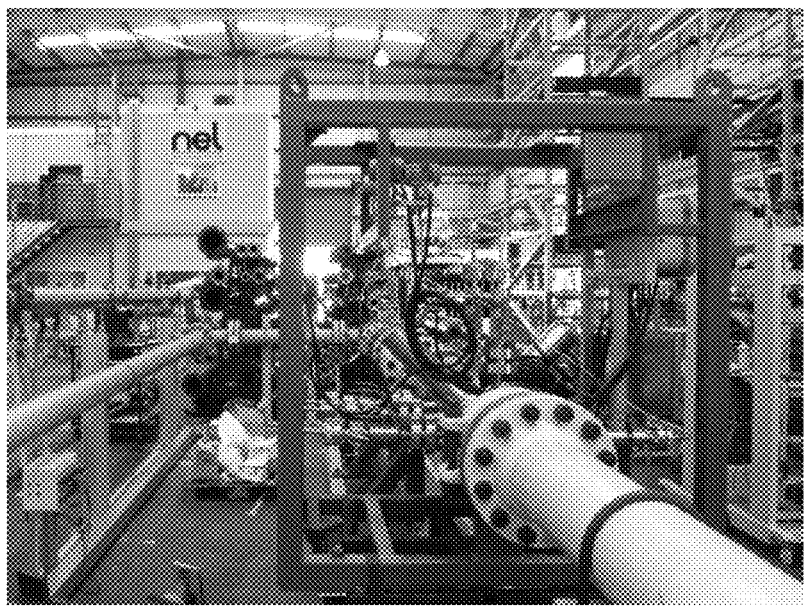
FIG. 6 shows the on-the-spot photograph of the sample machine of the device according to the invention when making measurements in English National Engineering Laboratory (NEL Laboratory).

To clearly show the relative measuring error of the flowrates of gas and liquid phases, the error data in Table 2 and Table 3 are plotted, as shown in FIGS. 4 and 5.

As seen from data in Tables 2 and 3 and FIG. 4 and FIG. 5, the use of the device and method of the invention not only can achieve the measurement of gas and liquid flowrates of wet gas in a horizontal pipeline, but also can achieve a very high measurement precision. After further corrections with the above "equal-diameter eccentric round model" and "slip model", the relative errors of the flowrates of the gas and liquid phases are greatly reduced, and particularly, the relative error of the liquid phase are reduced more obviously. Conventional devices and methods for measuring wet gas flowrates are incomparable to the invention. A huge difficulty in the wet gas measuring field resides in that measuring errors of the volume flowrate of the liquid phase is very high, because the proportion of the flowrate of the liquid phase in wet gas is small, for example, according to different amounts of moisture in the wet gas, less than 10%, or less than 5%, or less than 2%. That is, because the cardinal number is small, the value is particularly sensitive to measurement errors. According to general requirements of oil-gas manufacturers, it can be acceptable that the relative error of liquid volume flowrate is less than 20%, and thus the designing measurement errors of liquid volume flowrate in conventional devices and methods for measuring wet gas flowrate also fall into the range of ±20%. The errors before the correction shown in FIG. 4 and FIG. 5 also prove this point. While in the method of present invention, a relative error of the liquid flowrate within ±20% can achieved in both vertical radial direction and declining radial direction, which can prove that the device and method of the invention can replace devices and methods in the prior art. In addition, the applicant further make more experiments in the directions having an angle of 45°, 60°, etc., relative to the horizontal radial direction, and all corresponding results show that the relative error of the liquid flowrate is greatly lowered, and if in terms of the maximum relative error, it can fall into the range of ±14%, and if in terms of average error, it can fall into the range of ±7%.

The above examples can embody the feasibility of the device and method of the invention for measuring flowrates of gas phase and liquid phase in wet gas, and the device and method of the invention have the great advantage of greatly lowering the relative errors for measuring the flowrate of the liquid phase.

It should be pointed out that the examples illustratively use the combinations of the "equal-diameter eccentric round model" and "Haimo slip model" to conduct the measurements and data treatments; however, in fact, the invention has inventively used the "equal-diameter eccentric round model" to convert the measured gas linear phase fraction into a gas area phase fraction which is more close to the actual situation, and during the conversion of the area phase fraction into a volume phase fraction by subsequently using a slip difference model, it is obvious that other slip difference models also can be used. That is, the invention also can use the above "equal-diameter eccentric round model" in combination of other slip difference models according to needs, and the following basic objective of the invention can also be achieved: the online and precise measurement of the flowrates of gas phase and liquid phase in a wet gas is carried out in a horizontal pipe.

As compared with conventional flowrate meters, the measuring device and method of the invention have the following advantages:

1. The measurements of the flowrates of gas phase and liquid phase in a wet gas can be carried out in a horizontal Venturi tube, which can overcome the technical prejudice that the measurements must be carried out in a vertical pipeline.

2. The gamma ray monitor may be arranged along any radial direction at the throat of the horizontal Venturi tube, rather than limited to the vertical radial direction.

3. The measurement precision is increased. For example, as to the liquid flowrate, if in terms of the maximum relative error, it may be fall into the range of ±14%, and if in terms of the average error, it may be fall into the range of ±7%; as to the gas flowrate, if in terms of the maximum relative error, it may be fall into the range of ±3.6%, and if in terms of the average error, it may be fall into the range of ±2.9%. The precision reaches a maximum measuring precision level of wet gas flowrate meters in the world.

The above contents are merely used for illustrate the invention. Furthermore, a person skilled in the art can understand that all arrangement manners, specific numbers as listed out in the examples are merely illustrative. Thus, a person skilled in the art can change many details of the invention according to actual situations while no deviating the protection scope of the invention as defined by the claims. The protection scope of the invention is based on the expressions in the claims.

TABLE 2

Measurement results of flowrates of gas phase and liquid phases and relative errors thereof when gamma ray monitor make measurement in a vertical radial direction (θ = 90°) Diameter of Venturi throat = 100.04 mm, β = 0.582

| A testing point | B Liquid flowrate at working condition m3/h | C Gas flowrate at working condition m3/h | D Gas density at working condition kg/m3 | E liquid density at working condition kg/m3 | F Differential pressure kPa | G αg_90 % | H Measured liquid flowrate m3/h |
|---|---|---|---|---|---|---|---|
| 1 | 39.91 | 903.29 | 71.39 | 802.13 | 53.03 | 95.83 | 40.37 |
| 2 | 34.99 | 907.17 | 71.05 | 802.10 | 51.42 | 96.02 | 38.22 |
| 3 | 24.76 | 899.27 | 70.84 | 802.09 | 46.05 | 96.91 | 29.07 |
| 4 | 14.92 | 600.31 | 70.00 | 802.09 | 19.44 | 94.50 | 30.95 |
| 5 | 20.07 | 901.27 | 70.75 | 802.08 | 44.16 | 97.34 | 24.92 |
| 6 | 22.79 | 1200.82 | 71.79 | 802.07 | 76.90 | 98.34 | 21.37 |
| 7 | 10.01 | 599.58 | 69.75 | 802.02 | 17.91 | 95.84 | 23.54 |
| 8 | 14.96 | 900.03 | 70.47 | 802.08 | 41.43 | 97.92 | 19.39 |
| 9 | 14.95 | 1200.57 | 71.19 | 802.09 | 70.76 | 98.88 | 14.21 |
| 10 | 6.96 | 600.11 | 69.65 | 802.00 | 17.03 | 96.87 | 17.96 |
| 11 | 10.03 | 898.95 | 70.28 | 802.03 | 38.78 | 98.64 | 12.63 |
| 12 | 10.06 | 1196.24 | 70.97 | 802.02 | 66.34 | 99.24 | 9.48 |
| 13 | 6.95 | 900.00 | 70.12 | 802.01 | 37.19 | 99.12 | 8.25 |
| 14 | 3.99 | 600.63 | 69.48 | 801.51 | 16.17 | 98.22 | 10.58 |
| 15 | 7.03 | 1197.22 | 70.72 | 802.07 | 63.98 | 99.44 | 6.89 |
| 16 | 4.02 | 901.21 | 69.98 | 801.27 | 35.46 | 99.56 | 4.14 |
| 17 | 4.01 | 1200.41 | 70.63 | 801.20 | 62.09 | 99.75 | 3.05 |

| A testing point | I Measured gas flowrate m3/h | J Liquid flowrate corrected by the model and slip m3/h | K Gas flowrate corrected by the model and slip m3/h | L Gas flowrate relative error before correction % | M Liquid flowrate relative error before correction % | N Gas flowrate relative error after correction % | O Liquid flowrate relative error after correction % |
|---|---|---|---|---|---|---|---|
| 1 | 927.83 | 41.69 | 920.90 | 2.72 | 1.14 | 1.95 | 4.46 |
| 2 | 922.70 | 36.98 | 929.23 | 1.71 | 9.23 | 2.43 | 5.71 |
| 3 | 912.35 | 26.34 | 927.34 | 1.45 | 17.38 | 3.12 | 6.38 |
| 4 | 531.45 | 16.99 | 605.74 | −11.47 | 107.36 | 0.90 | 13.83 |
| 5 | 913.34 | 21.44 | 932.84 | 1.34 | 24.13 | 3.50 | 6.80 |
| 6 | 1263.37 | 23.85 | 1249.28 | 5.21 | −6.21 | 4.04 | 4.65 |
| 7 | 542.88 | 11.34 | 610.65 | −9.46 | 135.08 | 1.85 | 13.28 |
| 8 | 912.79 | 15.95 | 932.54 | 1.42 | 29.58 | 3.61 | 6.60 |
| 9 | 1252.91 | 15.58 | 1244.88 | 4.36 | −4.97 | 3.69 | 4.19 |
| 10 | 556.72 | 7.83 | 614.79 | −7.23 | 158.15 | 2.45 | 12.48 |
| 11 | 915.24 | 10.55 | 927.41 | 1.81 | 25.97 | 3.17 | 5.23 |
| 12 | 1240.25 | 10.42 | 1234.65 | 3.68 | −5.79 | 3.21 | 3.54 |
| 13 | 925.94 | 7.29 | 931.73 | 2.88 | 18.67 | 3.53 | 4.82 |
| 14 | 582.24 | 4.40 | 619.01 | −3.06 | 164.90 | 3.06 | 10.30 |
| 15 | 1234.50 | 7.26 | 1232.26 | 3.11 | −1.98 | 2.93 | 3.28 |

TABLE 2-continued

Measurement results of flowrates of gas phase and liquid phases and relative errors thereof when gamma ray monitor make measurement in a vertical radial direction ($\theta = 90°$) Diameter of Venturi throat = 100.04 mm, $\beta = 0.582$

| 16 | 928.91  | 4.16 | 928.83  | 3.07 | 3.17   | 3.07 | 3.47 |
| 17 | 1239.73 | 4.10 | 1233.24 | 3.28 | −24.14 | 2.74 | 2.24 |

TABLE 3

Measurement results of flowrates of gas phase and liquid phases and relative errors thereof when gamma ray monitor make measurement in a declining radial direction ($\theta = 30°$) Diameter of Venturi throat = 100.04 mm, $\beta = 0.582$

| A testing point | B Liquid flowrate at working condition m3/h | C Gas flowrate at working condition m3/h | D Gas density at working condition kg/m3 | E liquid density at working condition kg/m3 | F Differential pressure kPa | G $\alpha_g\_30$ % | H Measured liquid flowrate m3/h | I Measured gas flowrate m3/h |
|---|---|---|---|---|---|---|---|---|
| 1  | 39.91 | 903.29  | 71.39 | 802.13 | 53.03 | 96.93 | 30.98 | 978.04  |
| 2  | 34.99 | 907.17  | 71.05 | 802.10 | 51.42 | 97.26 | 27.64 | 979.88  |
| 3  | 24.76 | 899.27  | 70.84 | 802.09 | 46.05 | 98.02 | 19.52 | 965.68  |
| 4  | 14.92 | 600.31  | 70.00 | 802.09 | 19.44 | 98.64 | 8.96  | 651.79  |
| 5  | 20.07 | 901.27  | 70.75 | 802.08 | 44.16 | 98.39 | 15.82 | 964.97  |
| 6  | 22.79 | 1200.82 | 71.79 | 802.07 | 76.90 | 98.48 | 19.67 | 1273.14 |
| 7  | 10.01 | 599.58  | 69.75 | 802.02 | 17.91 | 99.16 | 5.44  | 645.59  |
| 8  | 14.96 | 900.03  | 70.47 | 802.08 | 41.43 | 98.79 | 11.71 | 957.35  |
| 9  | 14.95 | 1200.57 | 71.19 | 802.09 | 70.76 | 98.99 | 12.88 | 1260.75 |
| 10 | 6.96  | 600.11  | 69.65 | 802.00 | 17.03 | 99.42 | 3.75  | 639.35  |
| 11 | 10.03 | 898.95  | 70.28 | 802.03 | 38.78 | 99.13 | 8.28  | 940.86  |
| 12 | 10.06 | 1196.24 | 70.97 | 802.02 | 66.34 | 99.33 | 8.36  | 1246.94 |
| 13 | 6.95  | 900.00  | 70.12 | 802.01 | 37.19 | 99.39 | 5.73  | 941.16  |
| 14 | 3.99  | 600.63  | 69.48 | 801.51 | 16.17 | 99.08 | 5.67  | 611.35  |
| 15 | 7.03  | 1197.22 | 70.72 | 802.07 | 63.98 | 99.54 | 5.74  | 1241.48 |
| 16 | 4.02  | 901.21  | 69.98 | 801.27 | 35.46 | 99.65 | 3.27  | 934.30  |
| 17 | 4.01  | 1200.41 | 70.63 | 801.20 | 62.09 | 99.77 | 2.81  | 1241.21 |

| A testing point | J Liquid flowrate corrected by the model and slip m3/h | K Gas flowrate corrected by the model and slip m3/h | L Gas flowrate relative error before correction % | M Liquid flowrate relative error before correction % | N Gas flowrate relative error after correction % | O Liquid flowrate relative error after correction % |
|---|---|---|---|---|---|---|
| 1  | 43.24 | 912.85  | 8.28 | −22.39 | 1.06 | 8.34  |
| 2  | 38.06 | 923.54  | 8.02 | −21.00 | 1.80 | 8.78  |
| 3  | 26.84 | 924.57  | 7.39 | −21.19 | 2.81 | 8.41  |
| 4  | 15.60 | 613.53  | 8.58 | −39.96 | 2.20 | 4.52  |
| 5  | 21.72 | 931.24  | 7.07 | −21.20 | 3.32 | 8.21  |
| 6  | 24.84 | 1243.66 | 6.02 | −13.68 | 3.57 | 9.00  |
| 7  | 10.41 | 616.10  | 7.67 | −45.67 | 2.76 | 3.93  |
| 8  | 16.09 | 931.73  | 6.37 | −21.76 | 3.52 | 7.54  |
| 9  | 16.10 | 1241.85 | 5.01 | −13.86 | 3.44 | 7.65  |
| 10 | 7.23  | 618.32  | 6.54 | −46.11 | 3.03 | 3.95  |
| 11 | 10.70 | 926.54  | 4.66 | −17.46 | 3.07 | 6.70  |
| 12 | 10.69 | 1233.03 | 4.24 | −16.88 | 3.08 | 6.24  |
| 13 | 7.40  | 931.07  | 4.57 | −17.57 | 3.45 | 6.41  |
| 14 | 4.40  | 619.00  | 1.79 | 41.95  | 3.06 | 10.33 |
| 15 | 7.41  | 1231.36 | 3.70 | −18.36 | 2.85 | 5.40  |
| 16 | 4.23  | 928.40  | 3.67 | −18.69 | 3.02 | 5.23  |
| 17 | 4.17  | 1232.81 | 3.40 | −30.12 | 2.70 | 4.00  |

What is claimed is:

1. A device for online measurement of gas flowrate of a gas phase and liquid flowrate of a wet gas phase in a horizontal pipe, comprising:

A horizontal Venturi tube, comprising a truncated cone-shaped inlet pipesection with cross-section area reduced gradually, a cylindrical throat pipesection and a truncated cone-shaped outlet pipesection with cross-section area increased gradually; and A gamma ray monitor, comprising a gamma ray emitter and a gamma ray detector arranged in a manner that gamma rays emitted by the gamma ray emitter radially pass through the cross-section of the throat pipesection to reach the gamma ray detector, wherein the device does not include physical apparatus for assuring complete stratification of the gas phase and wet gas phase.

2. The device according to claim 1, further comprising a total volume flowrate metering device located upstream or downstream of the horizontal Venturi tube.

3. The device according to claim 1, wherein the gamma ray monitor measures in a fixed radial direction or in a variable radial direction.

4. The device according to claim 1, wherein an angle θ between said radial direction and a horizontal radial direction may be one selected from the group of: θ≥10°, θ≥15°, θ≥30°, θ≥45°, θ≥60°, θ≥75°, θ≥80°, θ≥85°, and θ=90°.

5. The device according to claim 1, wherein the total volume flowrate metering device is selected from the group consisting of an elbow flowrate meter, a Venturi flowrate meter, a ratometer, a float flowrate meter, and an orifice flowrate meter; alternatively, the total volume flowrate metering device is a flow velocity measuring device.

6. The method according to claim 1, further comprising a differential pressure measuring component for measuring the pressure difference between the upstream and the throat of the Venturi tube, a pressure measuring component for measuring the pressure of flow at the upstream of the Venturi tube, and a temperature measuring component for measuring the temperature of the wet gas.

7. A method for online measurement of gas flowrate and liquid flowrate of a wet gas in a horizontal pipe, comprising:

a. passing the wet gas through a device comprising a segment of a horizontal Venturi tube, the horizontal Venturi pipe comprising a truncated cone-shaped inlet pipesection with cross section area reduced gradually, a cylindrical throat pipesection and a truncated cone-shaped outlet pipesection with cross section area increased gradually, wherein the device does not include physical apparatus for assuring complete stratification of the gas phase and wet gas phase;

b. measuring radial linear phase fractions $\alpha_{g\text{-}\theta}$ of the gas phase along the cross section of the throat pipesection with a gamma ray monitor, the gamma ray monitor comprising a gamma ray emitter and a gamma ray detector arranged in a manner that gamma rays emitted by the gamma ray emitter can radially pass through the cross section of the throat pipesection to reach the gamma ray detector; and c. calculating gas phase flowrate $Q_g$ and liquid phase flowrate $Q_l$ with a total volume flowrate $Q_t$ and the above radial linear phase fractions $\alpha_{g\text{-}\theta}$ of the gas phase in accordance with an equal-diameter eccentric round model with the following specific equations:

calculation of an eccentric distance d:

$$d = (R - 2R\alpha_{g\text{-}\theta})\sin\theta + \sqrt{R^2 - (R - 2R\alpha_{g\text{-}\theta})^2 \cos^2\theta}$$

wherein R denotes a radius of the throat pipesection, and θ denotes an angle of the radial direction used during the measurement relative to the horizontal radial direction;

calculation of an area phase fraction $\alpha_{sg}$ of the gas phase:

$$\alpha_{sg} = \frac{4R^2 \cos^{-1}\left(\frac{d}{2R}\right) - \sqrt{(4R^2 - d^2)d^2}}{2\pi R^2};$$

calculation of a volume phase fraction GVF of the gas phase:

$$GVF = \frac{\alpha_{sg} \times S}{\alpha_{sg} \times S + 1 - \alpha_{sg}}$$

wherein S denotes a slip factor between the gas phase and liquid phase; when the slip difference is taken into account, S is calculated by using experimental equations; when the slip difference is not taken into account, S=1, so GVF=$\alpha_{sg}$;

calculation of gas and liquid flowrates of the wet gas in the horizontal pipe:

$Q_g = Q_t \times GVF$ $Q_l = Q_t \times (1 - GVF)$.

8. The method according to claim 7, wherein the total volume flowrate $Q_t$ is measured by the total volume flowrate metering device located upstream or downstream of the horizontal Venturi tube.

9. The method according to claim 7, wherein when a differential pressure measuring component for measuring the pressure difference between the upstream and the throat of the Venturi tube, a pressure measuring component for measuring the pressure of flow upstream of the Venturi tube, and a temperature measuring component for measuring the temperature of the wet gas are used, the total volume flowrate $Q_t$ may be calculated according to the following equation:

$$Q_t = C \cdot \frac{\pi d^2}{4} \cdot \frac{1}{\sqrt{1 - \beta^4}} \cdot \sqrt{2 \cdot (\Delta P / \rho_{mix})}, \, m^3/s$$

wherein C denotes the efflux coefficient of the fluid, dimensionless; d denotes an inner diameter of the throat pipesection of the Venturi tube; β denotes a ratio of the inner diameter of the throat pipesection of the Venturi tube to an inner diameter of the pipe at an inlet of the Venturi tube; ΔP denotes a pressure difference measured by the differential pressure measuring component; $\rho_{mix}$ is a mixed density of the wet gas; and each of the unit of individual physical parameters using international units.

10. The method according to claim 7, wherein the experimental equation for calculating the slip factor S may be one selected from the following models: Momentum Flux Model, Smith Model, Chrisholm Model and Haimo Slip Model.

11. The method according to claim 7, wherein the experimental equation for calculating the slip factor S may be Haimo Model.

* * * * *